United States Patent
Goldmann et al.

(10) Patent No.: US 6,987,185 B2
(45) Date of Patent: Jan. 17, 2006

(54) METHOD FOR SEPARATING METHYL 4-(2-CHLORO-4-FLUOROPHENYL)-2-(3,5-DIFLUORO-2-PYRIDINYL)-6-METHYL-1,4-DIHYDRO-5-PYRIMIDINE-CARBOXYLATE-RECEMATE

(75) Inventors: Siegfried Goldmann, Wuppertal (DE); Peter Fey, Wuppertal (DE)

(73) Assignee: Bayer HealthCare AG, Leverkusen (DE)

( * ) Notice: Subject to any disclaimer, the term of this patent is extended or adjusted under 35 U.S.C. 154(b) by 14 days.

(21) Appl. No.: 10/478,602

(22) PCT Filed: May 15, 2002

(86) PCT No.: PCT/EP02/05339

§ 371 (c)(1),
(2), (4) Date: Jul. 15, 2004

(87) PCT Pub. No.: WO02/094807

PCT Pub. Date: Nov. 28, 2002

(65) Prior Publication Data

US 2004/0242878 A1 Dec. 2, 2004

(30) Foreign Application Priority Data

May 23, 2001 (DE) .......................... 101 25 131

(51) Int. Cl.
*C07D 401/04* (2006.01)

(52) U.S. Cl. ...................................................... 544/333

(58) Field of Classification Search .................. 544/333
See application file for complete search history.

(56) References Cited

U.S. PATENT DOCUMENTS

| 6,696,451 B1 | 2/2004 | Stoltefuss et al. | 514/256 |
| 2004/0167135 A1 | 8/2004 | Stoltefuss et al. | 514/256 |

FOREIGN PATENT DOCUMENTS

| EP | 1080086 | 7/2001 |
| WO | 0058302 | 5/2000 |

*Primary Examiner*—Patricia L. Morris

(57) ABSTRACT

The enantiomers of methyl 4-(2-chloro-4-fluorophenyl)-2-(3,5-difluoro-2-pyridinyl)-6-methyl)-1,4-dihydro-5-pyrimidinecarboxylate can be separated with the aid of (−)-camphanic acid.

5 Claims, No Drawings

METHOD FOR SEPARATING METHYL 4-(2-CHLORO-4-FLUOROPHENYL)-2-(3,5-DIFLUORO-2-PYRIDINYL)-6-METHYL-1,4-DIHYDRO-5-PYRIMIDINE-CARBOXYLATE-RECEMATE

The invention relates to a method for separating the enantiomeric methyl 4-(2-chloro-4-fluorophenyl)-2-(3,5-difluoro-2-pyridinyl)-6-methyl-1,4-dihydro-5-pyrimidinecarboxylates with the aid of (−)-camphanic acid.

The compound methyl 4-(2-chloro-4-fluorophenyl)-2-(3,5-difluoro-2-pyridinyl)-6-methyl-1,4-dihydro-5-pyrimidinecarboxylate corresponds to the formula

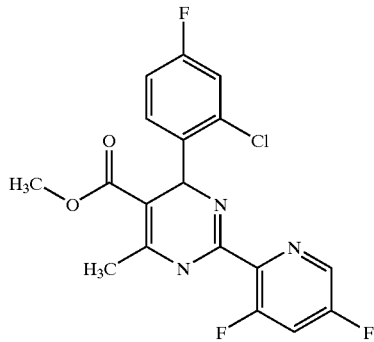

It is able to act as HBV core protein inhibitor and is suitable for the prophylaxis and treatment of hepatitis, especially hepatitis B. The compound and various methods for preparing it are disclosed in EP-A 1 080 086 (example 61). The preferred optically active form is the (−)-enantiomer. The enantiomers can be separated on chiral columns. Although this method leads to good results, its suitability for industrial production is low.

It has now been found that the two enantiomeric methyl 4-(2-chloro-4-fluorophenyl)-2-(3,5-difluoro-2-pyridinyl)-6-methyl-1,4-dihydro-5-pyrimidinecarboxylates can be separated via their diastereomeric (−)-camphanic salts; this is because the (−)-camphanic salt of the (R) enantiomer is less soluble than the (−)-camphanic salt of the (L) enantiomer in many solvents. The term "salts" also includes for the purposes of this invention cocrystallized products; according to the NMR spectrum, the base is present mainly in unprotonated form.

The invention therefore relates to a method for separating the enantiomeric methyl 4-(2-chloro-4-fluorophenyl)-2-(3,5-difluoro-2-pyridinyl)-6-methyl-1,4-dihydro-5-pyrimidinecarboxylates with the aid of (−)-camphanic acid.

The difference in solubility of the diastereomeric salts can be utilized in principle for two different types of separation thereof: firstly by (fractional) crystallization of the less soluble diastereomer from solution or secondly by dissolving the more soluble diastereomer out of the mixture of the solid diastereomers.

The procedure is thus usually such that (−)-camphanic acid and the racemate to be separated are reacted to give the corresponding diastereomeric salts and either a) the reaction product is dissolved and the less soluble product is induced to precipitate by cooling the solution and/or partially stripping off the solvent, and the precipitated product is separated from the solution or b) the solid reaction product is treated with solvent in order to dissolve the more soluble product and to separate this solution from the less soluble residue.

The term "solvent" includes for the purposes of the invention all conventional solvents, e.g. hydrocarbons such as benzene, xylene, toluene, hexane, cyclohexane or petroleum fractions, halohydrocarbons such as dichloromethane, trichloromethane, tetrachloromethane, trichloroethane, tetrachloroethane, 1,2-dichloroethane or trichloroethylene, alcohols such as methanol, ethanol, n-propanol, isopropanol, n-butanol or tert-butanol, ethers such as diethyl ether, methyl isopropyl ether, diisopropyl ether, glycol monomethyl ether, glycol dimethyl ether, diethylene glycol dimethyl ether, tetrahydrofuran, dioxane, ketones such as acetone, methyl ethyl ketone, carboxylic acids such as glacial acetic acid, esters such as ethyl acetate and butyl acetate, heterocycles such as pyridine or aprotic solvents such as nitromethane, acetonitrile, dimethylformamide, dimethyl sulfoxide and hexamethylphosphoric triamide and mixtures of said compounds. It is also possible where appropriate to add water to water-miscible organic solvents. Preferred solvents for the reaction of the racemate to be separated with (−)-camphanic acid are alcohols, especially ethanol; preferred solvents for separating the diastereomeric salts are ethers, esters and ketones, especially diisopropyl ether.

The dissolving of the diastereomer can take place within a wide temperature range; preferably at the boiling point of the solvent down to 20° C. The temperatures during the crystallization of the less soluble diastereomerically pure salt or during the washing out of the more soluble diastereomerically pure salt can also lie within a wide range; it is preferably −40 to 20° C., preferably about 0° C.

The liberation of the free enantiomer from the diastereomerically pure salt can take place with any conventional base such as ammonia, alkali metal hydroxides such as sodium or potassium hydroxide, alkali metal carbonates or bicarbonates such as sodium or potassium carbonate or bicarbonate. The pure enantiomer can then be extracted from the basic aqueous solution directly with an organic solvent.

The (−)-camphanic acid can be precipitated by acidifying the aqueous solution thereof and then be reused.

The invention further relates to D- and L-methyl 4-(2-chloro-4-fluorophenyl)-2-(3,5-difluoro-2-pyridinyl)-6-methyl-1,4-dihydro-5-pyrimidinecarboxylate (−)-camphanic acid salt.

EXAMPLE

Racemate Resolution with (−)-Camphanic Acid
(−)-Methyl (4R)-4-(2-chloro-4-fluorophenyl)-2-(3,5-difluoro-2-pyridinyl)-6-methyl-1,4-dihydro-5-pyrimidinecarboxylate

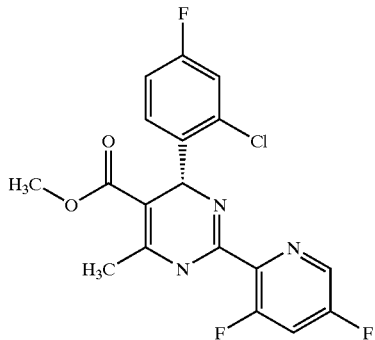

37.68 g (95.21 mmol) of methyl 4-(2-chloro-4-fluorophenyl)-2-(3,5-difluoro-2-pyridinyl)-6-methyl-1,4-dihydro-5-pyrimidinecarboxylate and 18.87 g (95.21 mmol) of (−)-camphanic acid were dissolved in boiling ethanol. After cooling, the ethanol was evaporated off to dryness; the residue was broken up, mixed with diisopropyl ether and heated to the reflux temperature. After cooling to 0° C. and standing overnight, the crystals were filtered off with suction and washed with cold diisopropyl ether. The filter cake was suspended in ethyl acetate, made alkaline with 10% by weight aqueous sodium carbonate solution and extracted twice with ethyl acetate. The organic phases were dried with sodium sulfate and evaporated. The residue was crystallized with a little cold ethanol. 17.7 g (93.7%) of methyl 4-(2-chloro-4-fluorophenyl)-2-(3,5-difluoro-2-pyridinyl)-6-methyl-1,4-dihydro-5-pyrimidinecarboxylate (ee 97%, HPLC) were obtained.

The absolute configuration (R) was determined by x-ray investigation.

What is claimed is:

1. A method for resolving a mixture of the enantiomers of methyl 4-(2-chloro-4-fluorophenyl)-2-(3,5-difluoro-2-pyridinyl)-6-methyl-1,4-dihydro-5-pyrimidinecarboxylate comprising the steps of adding (−)-camphanic acid to form a mixture of diastereomeric (−)-camphanic salts, and separating said salts.

2. The method as claimed in claim 1, wherein the (−)-camphanic acid salts of (D/L)-methyl 4-(2-chloro-4-fluorophenyl)-2-(3,5-difluoro-2-pyridinyl)-6-methyl-1,4-dihydro-5-pyrimidinecarboxylate are separated by crystallization, and each enantiomer is liberated with base, and isolated where appropriate, from the removed solid (−)-camphanic acid salt and/or from the removed solution.

3. The method as claimed in claim 1, wherein the more soluble diastereomer is dissolved out of the mixture of the (−)-camphanic acid salts of (D/L)-methyl 4-(2-chloro-4-fluorophenyl)-2-(3,5-difluoro-2-pyridinyl)-6-methyl-1,4-dihydro-5-pyrimidinecarboxylate, the resulting solution is separated from the less soluble diastereomer, and each enantiomer is liberated with base, and isolated where appropriate, from the removed solid (−)-camphanic acid salt and/or from the removed solution.

4. D-Methyl 4-(2-chloro-4-fluorophenyl)-2-(3,5-difluoro-2-pyridinyl)-6-methyl-1,4-dihydro-5-pyrimidinecarboxylate (−)-camphanic acid salt.

5. L-Methyl 4-(2-chloro-4-fluorophenyl)-2-(3,5-difluoro-2-pyridinyl)-6-methyl-1,4-dihydro-5-pyrimidinecarboxylate (−)-camphanic acid salt.

* * * * *